(12) United States Patent
Kurihara (10) Patent No.: US 8,048,052 B2
(45) Date of Patent: Nov. 1, 2011

(54) ABSORPTIVE ARTICLE

(75) Inventor: Ryoko Kurihara, Sakura (JP)

(73) Assignee: Daio Paper Corporation, Ehime (JP)

( * ) Notice: Subject to any disclaimer, the term of this patent is extended or adjusted under 35 U.S.C. 154(b) by 0 days.

(21) Appl. No.: 12/919,698

(22) PCT Filed: Feb. 26, 2009

(86) PCT No.: PCT/JP2009/053493
§ 371 (c)(1),
(2), (4) Date: Sep. 14, 2010

(87) PCT Pub. No.: WO2009/107695
PCT Pub. Date: Sep. 3, 2009

(65) Prior Publication Data
US 2011/0004179 A1 Jan. 6, 2011

(30) Foreign Application Priority Data
Feb. 26, 2008 (JP) .................... 2008-043890

(51) Int. Cl.
*A61F 13/15* (2006.01)
(52) U.S. Cl. ......... 604/385.14; 604/385.01; 604/385.04; 604/385.17
(58) Field of Classification Search ............. 604/385.01, 604/385.03–385.05, 385.11, 385.14, 385.17
See application file for complete search history.

(56) References Cited

U.S. PATENT DOCUMENTS

| 5,514,104 | A | * | 5/1996 | Cole et al. ............... 604/366 |
| 6,652,498 | B1 | | 11/2003 | Glasgow et al. |
| 6,652,499 | B1 | | 11/2003 | Edgren et al. |
| 6,863,664 | B2 | * | 3/2005 | Wada et al. ............ 604/385.17 |
| 2002/0143309 | A1 | * | 10/2002 | Glasgow et al. ......... 604/378 |
| 2003/0125694 | A1 | * | 7/2003 | Motta et al. ............ 604/385.04 |
| 2005/0080391 | A1 | * | 4/2005 | Yoshimasa et al. ...... 604/385.01 |
| 2005/0124953 | A1 | * | 6/2005 | Woltman et al. ........ 604/385.01 |

FOREIGN PATENT DOCUMENTS

| JP | 5-024025 | 3/1993 |
| JP | 2000-189459 | 7/2000 |
| JP | 2001-314439 | 11/2001 |
| JP | 2002-524148 | 8/2002 |
| JP | 2006-034495 | 2/2006 |

* cited by examiner

*Primary Examiner* — Lynne Anderson
(74) *Attorney, Agent, or Firm* — Jordan and Hamburg LLP (57) ABSTRACT

A sanitary napkin is constituted of napkin main body composed of a top sheet, a liquid-impermeable bottom sheet, and an absorber interposed therebetween; and a napkin sub-body joined to the upper layer of the napkin main body and similarly composed. The napkin sub-body is constituted of a front portion that is joined to the napkin main body at a bleeding port-corresponding region and a back portion that is positioned behind the front portion and can be divided into right and left parts at a dividing line formed along the longitudinal direction from the back end of the center in the width direction of the sanitary napkin such that, to provide hip-holding flaps, the divided right and left parts can spread outward in the width direction of the napkin main body from the boundary between the front portion and the back portion at which the base end of the dividing line is located.

3 Claims, 11 Drawing Sheets

ABSORPTIVE ARTICLE

BACKGROUND OF THE INVENTION

The present invention relates to an absorptive article such as a sanitary napkin, a pantiliner, or an incontinence pad for absorbing menstrual blood, vaginal discharge, or the like and, specifically, relates to an absorptive article having hip-holding flaps that can be optionally adjusted in size.

Absorptive articles, such as sanitary napkins, pantiliners, vaginal discharge sheets, and incontinence pads, conventionally known are those each having a liquid-impermeable bottom sheet of a polyethylene sheet, a polyethylene laminated nonwoven fabric, or the like, a liquid-permeable top sheet of a nonwoven fabric, a porous plastic sheet, or the like, and an absorber composed of cotton-like pulp or the like interposed therebetween.

In this kind of absorptive article, as disclosed in the following Patent Documents JP-A-200-189459 and JP-A-2006-34495, a hip-holding flap composed of a top material, a bottom material, and an absorber layer interposed therebetween is formed for preventing leakage from the buttock area.

SUMMARY OF INVENTION

However, in the absorptive articles disclosed in the above-mentioned Patent Documents 1 and 2, the sizes of the hip-holding flaps are defined, and a user cannot optionally adjust the size. Therefore, the hip-holding flap portion does not fit to the body of the user or the size of shorts, which causes problems, such as twists of hip-holding flaps, uncomfortable feeling, and also leakage of body fluid.

Accordingly, it is a primary object of the present invention to provide an absorptive article that is improved in fitting to a body and prevents body fluid leakage by enabling optional adjustment of the size of its hip-holding flap.

In order to solve the above-mentioned problems, the present invention according to a first aspect provides an absorptive article including an absorptive article main-body composed of a top sheet, a liquid-impermeable bottom sheet, and an absorber interposed therebetween; and an absorptive article sub-body joined to the upper layer of the absorptive article main-body and composed of a top sheet, a bottom sheet, and an absorber interposed therebetween, wherein the absorptive article sub-body is constituted of a front portion that is joined to the absorptive article main-body at a bleeding port-corresponding region and a back portion that is positioned behind the front portion and can be divided into right and left parts at a dividing line formed along the longitudinal direction from the back end of the center in the width direction of the absorptive article such that the divided right and left parts can spread outward in the width direction of the absorptive article main-body from the boundary between the front portion and the back portion at which the base end of the dividing line is located.

The invention of the first aspect relates to the absorptive article having the absorptive article sub-body composed of the front portion and the back portion joined to the upper layer of the absorptive article main-body at the front portion. The back portion is positioned behind the front portion and can be divided into right and left parts at a dividing line formed along the longitudinal direction from the back end of the center in the width direction of the absorptive article such that the divided right and left parts can spread outward in the width direction of the absorptive article main-body from the boundary between the front portion and the back portion as the base end. That is, when a user puts on the absorptive article, hip-holding flaps are formed by spreading the right and left parts of the back portion toward the respective outsides in the width direction of the absorptive article from the boundary between the front portion and the back portion at which the base end of the dividing line is located, and the size of the hip-holding flaps can be optionally adjusted by suitably adjusting the degree of spreading. Therefore, the size of the hip-holding flaps can be optionally adjusted so as to fit to the body of the user or the size of shorts, which improves fitting to the body and prevents body fluid from leaking.

Furthermore, by spreading the right and left parts of the back portion toward the respective outsides in the width direction of the absorptive article, wrinkle-like protrusions are formed at the boundary between the front portion and the back portion, from the base end of the dividing line to both side edges of the boundary between the front portion and the back portion. The formation of such protruding lines can block diffusion of menstrual blood or the like from the front portion to the back portion and thereby effectively prevents leakage from the back.

The present invention according to a second aspect provides the absorptive article of the first aspect, wherein the back portion has an approximately elliptical shape of which the long axis is in the front-back direction in the state that the right and left parts are arranged to face each other (i.e., unspread state).

In the invention of the second aspect, the back portion has an approximately elliptical shape of which the long axis is in the front-back direction in the state that the right and left parts are arranged to face to each other so that the right and left parts of the back portion fit along the buttock lines when the hip-holding flaps are formed by spreading the right and left parts toward the respective outsides in the width direction of the absorptive article.

The present invention according to a third aspect provides the absorptive article of the first or second aspect, wherein the back portion has a shape in which approximately the same width in the width direction is maintained in the region near the back end of the back portion in the state that the right and left parts are arranged to face to each other.

In the invention of the third aspect, the back portion has a shape having approximately the same width in the width direction in the region near the back side in the state that the right and left parts are arranged to face to each other so that the hip-holding flaps formed when the absorptive article is put on have large areas thereby to give a large absorptive area due to the hip-holding flaps and to prevent leakage of menstrual blood or the like.

The present invention according to a fourth aspect provides the absorptive article of any one of the first to third aspects, wherein the right and left parts of the back portion are each provided with a pinching tab extending toward the respective outsides.

In the invention of the fourth aspect, the right and left parts of the back portion are provided with the pinching tabs extending toward the respective outsides so that a user can easily spread the right and left parts when the user puts on the absorptive article.

The present invention according to a fifth aspect provides the absorptive article of any one of the first to fourth aspects, wherein the boundary between the front portion and the back portion is provided with incisions from both sides toward the inside in the width direction of the absorptive article.

In the invention of the fifth aspect, the boundary between the front portion and the back portion is provided with the incisions from both sides toward the inside in the width direction of the absorptive article so that the front portion and the back portion overlap each other without forming the aforementioned protrusions when the right and left parts of the back portion are spread, which can decrease uncomfortable feeling given to a user while maintaining the function of blocking menstrual blood or the like.

The present invention according to a sixth aspect provides the absorptive article of any one of the first to fifth aspect, wherein the bottom sheet of the absorptive article sub-body is constituted of a liquid-permeable material provided to the entire area of the front portion and a liquid-impermeable material provided to the entire or a part of the area of the back portion.

The present invention according to a seventh aspect provides the absorptive article of any one of the first to fifth aspect, wherein the bottom sheet of the absorptive article sub-body is constituted of a liquid-permeable material provided to the entire areas of the front portion and the back portion and a liquid-impermeable material provided to at least a part of the area of the back portion to form an under layer of the liquid-permeable material.

In the inventions of the sixth and seventh aspects, as the bottom sheet of the absorptive article sub-body, the liquid-impermeable material is provided to the entire or a part of the area of the back portion, and the liquid-permeable material is provided to at least the area other than the above area. Therefore, the hip-holding flaps absorb menstrual blood or the like overflowed from the absorptive article main-body and prevent it from exuding to shorts. In the invention of the sixth aspect, the liquid-permeable material and the liquid-impermeable material are joined together without overlapping each other to form the bottom sheet in a substantially unified manner. In the invention of the seventh aspect, the liquid-permeable material is provided to the entire area, and the liquid-impermeable material is joined to the liquid-permeable material at least in apart of the back portion to form a lower layer. Thus, the bottom sheet is formed in a substantially unified manner.

The present invention according to an eighth aspect provides the absorptive article of the sixth or seventh aspect, wherein the liquid-impermeable material is provided to the back portion at least in the areas that will be located laterally outside the absorptive article main-body when the right and left parts are spread toward the respective outsides in the width direction of the absorptive article.

The invention of the eighth aspect defines a specific configuration when the back portion is partially provided with the liquid-impermeable material. The liquid-impermeable material is provided to at least the areas that will be located laterally outside the absorptive article main-body in the state that the right and left parts are spread toward the respective outsides in the width direction of the absorptive article. By doing so, menstrual blood or the like absorbed by the absorptive article sub-body is prevented from exuding to shorts even in the state that the right and left parts are spread toward the outsides in the width direction of the absorptive article, and also body liquid is not prevented from being absorbed by the absorptive article main-body in the other regions. Therefore, the absorber of the absorptive article main-body can be effectively used in a large range.

The present invention according to a ninth aspect provides the absorptive article of anyone of the first to eighth aspects, wherein the bottom sheet of the back portion is provided with a plurality of strips of adhesive for letting the bottom sheet adhere to the absorptive article main-body and shorts.

In the invention of the ninth aspect, the bottom sheet of the back portion is provided with the plurality of adhesive strips for letting the bottom sheet adhere to the absorptive article main-body and shorts so that the absorptive article can be fixed in the state that the right and left parts of the back portion are spread.

The present invention according to a tenth aspect provides the absorptive article of the ninth aspect, wherein a release material covering the adhesive layers is joined in a unified manner to an individual packaging material for individually packaging the absorptive article.

In the invention of the tenth aspect, the release material covering the adhesive layers is joined in a unified manner to the individual packaging material for individually packaging the absorptive article so that the release material can be smoothly removed from the individually packaged state in one step.

According to the present invention described in detail above, provided is an absorptive article having hip-holding flaps that can be optionally adjusted in size therefore to improve fitting to the body and prevent body fluid from leaking.

DETAILED DESCRIPTION OF THE INVENTION

Figure 1:
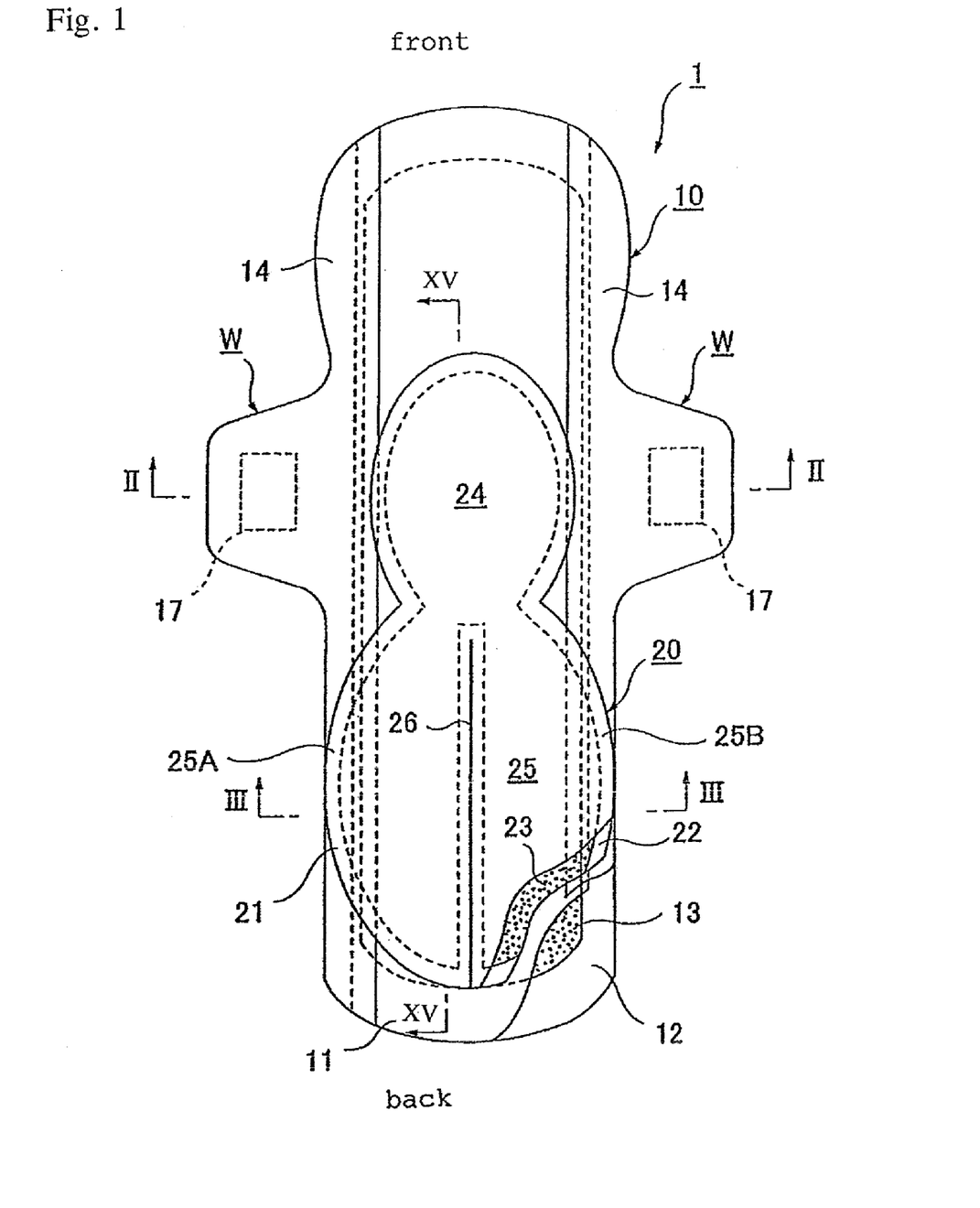
FIG. 1 is a partially broken developed view of a sanitary napkin 1 according to the present invention.
Figure 2:
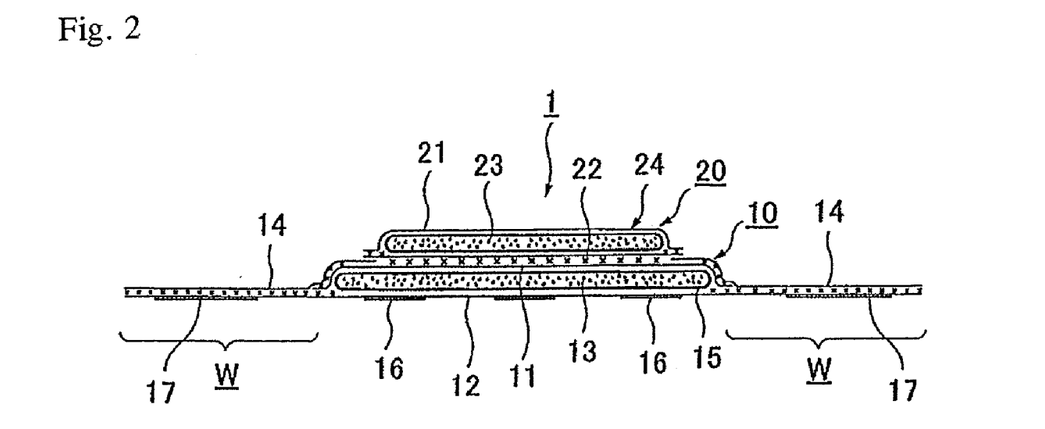
FIG. 2 is a fragmentary view taken along the line II-II of FIG. 1.
Figure 3:
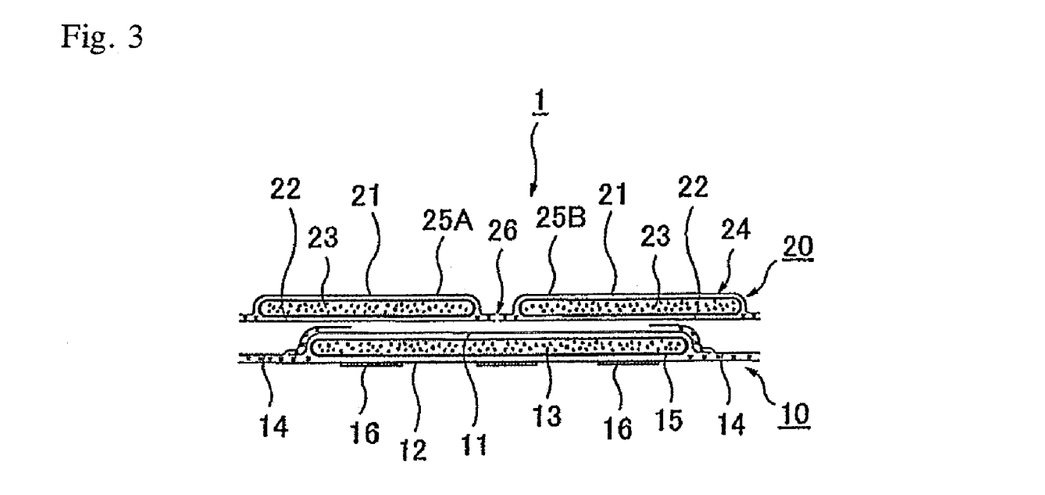
FIG. 3 is a fragmentary view taken along the line III-III of FIG. 1.
Figure 4:
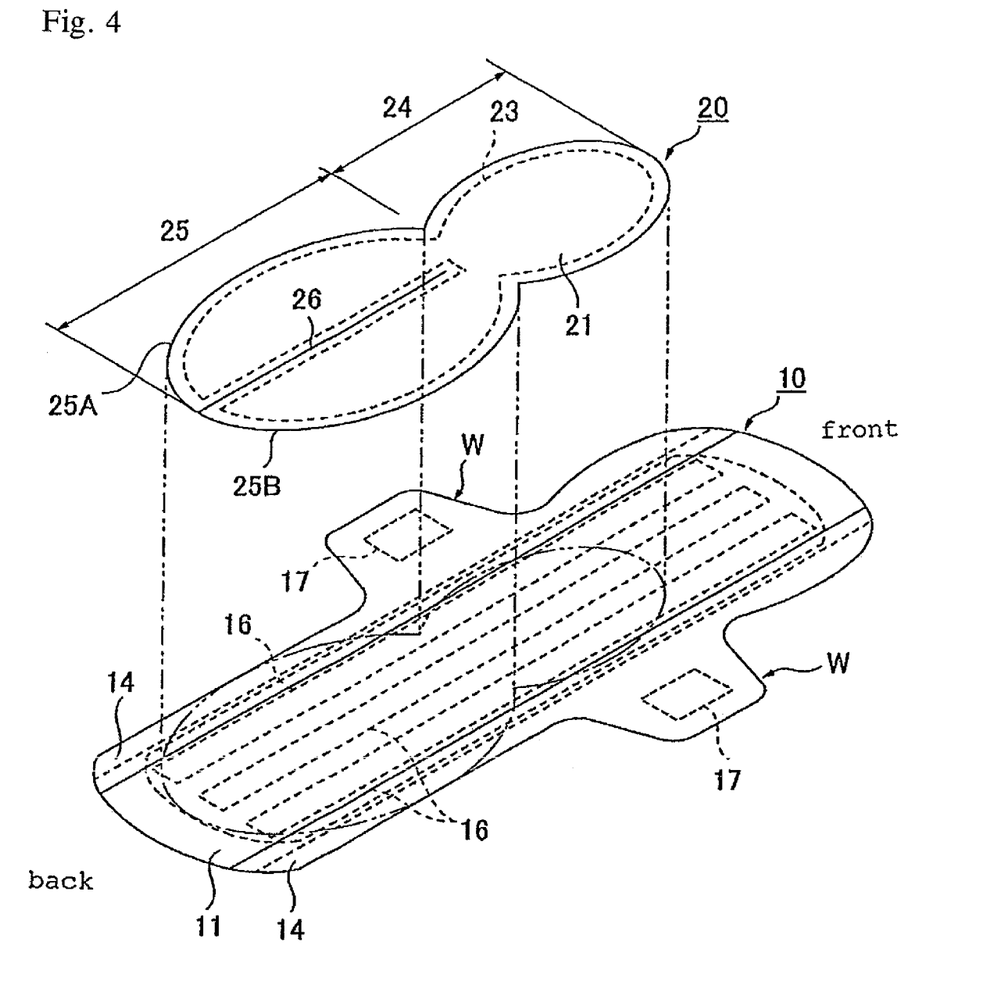
FIG. 4 is an exploded view of the sanitary napkin 1.

Embodiments of the present invention will now be described in detail with reference to the drawings. FIG. 1 is a partially broken developed view of a sanitary napkin 1 according to the present invention. FIG. 2 is a fragmentary view taken along the line II-II of FIG. 1, and FIG. 3 is a fragmentary view taken along the line III-III of FIG. 1. FIG. 4 is an exploded view of the sanitary napkin 1.

In the sanitary napkin 1, a napkin sub-body 20 composed of a top sheet 21, a bottom sheet 22, and an absorber 23 interposed therebetween is joined to the upper layer of a napkin main body 10 composed of a top sheet 11, a liquid-impermeable bottom sheet 12, and an absorber 13 interposed therebetween.

[Structure of Napkin Main Body 10]

The napkin main body 10 is composed of a liquid-impermeable bottom sheet 12 such as a polyethylene or polypropylene sheet; a liquid-permeable top sheet 11 allowing prompt permeation of menstrual blood, vaginal discharge, or the like; an absorber 13 interposed between both sheets 11 and 12 and made of cotton pulp, synthetic pulp, or the like; and side nonwoven fabrics 14, 14 respectively formed on the top both sides along the longitudinal direction. Furthermore, in the side edges of the napkin main body 10 in the longitudinal direction, the bottom sheet 12 and the side nonwoven fabric 14 are bonded to each other to form wing-like flaps W, W that protrude sideward and are fixed to an undergarment so as to retain the crotch portion of the sanitary napkin 1 at the crotch portion of an undergarment when it is put on. Incidentally, the absorber 13 can be surrounded by crepe paper 15 for maintaining the shape and increasing the diffusibility.

In the circumference of the absorber 13, the outer edges of the liquid-impermeable bottom sheet 12 are bonded to the liquid-permeable top sheet 11 at the front and back edges with an adhesive such as hot melt or by adhesion means such as heat sealing, and a portion of the liquid-impermeable bottom sheet 12 protruding sideward from the absorber 13 is joined to the side nonwoven fabrics 14 at both side edges with an adhesive such as hot melt or by adhesion means such as heat sealing.

The structure of the napkin main body 10 will be described in detail below:

The liquid-impermeable bottom sheet 12 is made of a sheet material having at least a water-sealing property, for example, a resin sheet of an olefin-based resin such as polyethylene or polypropylene, but may be made of a laminated nonwoven fabric where a nonwoven fabric is laminated to polyethylene or the like or a nonwoven fabric sheet substantially provided with liquid impermeability by interposing a waterproof film (in this case, the waterproof film and the nonwoven fabric constitute a liquid-impermeable bottom sheet). Recently, from the viewpoint of preventing a damp feeling, a material having moisture permeability tends to be used. Such a water-sealing and moisture-permeable sheet material is obtained as a micro-porous sheet by melt-kneading an inorganic filler in an olefin-based resin such as polyethylene or polypropylene and forming it into a sheet and then uniaxially or biaxially extending the sheet.

The liquid-permeable top sheet 11 is preferably made of, for example, a porous or nonporous nonwoven fabric or a porous plastic sheet. As a fibrous base material constituting the nonwoven fabric, a recycled fiber such as rayon or cupra or a natural fiber such as cotton can be used, in addition to synthetic fiber such as olefin-based (such as polyethylene and polypropylene), polyester-based, and polyamide-based synthetic fiber. The nonwoven fabric can be obtained by an arbitrary processing method such as spunlacing, spunbonding, thermal bonding, melt blowing, or needle punching. Among these processing methods, the spunlacing is excellent in flexibility, the spunbonding is excellent in drape forming, and the thermal bonding and air-through bonding are excellent in bulk and softness.

The absorber 13 interposed between the liquid-impermeable bottom sheet 12 and the liquid-permeable top sheet 11 is constituted of, for example, fluff-like pulp and a water-absorbing polymer. The water-absorbing polymer is mixed in the pulp constituting the absorber in a form of granular powder, for example. Examples of the pulp include chemical pulp made from wood and those composed of cellulose fiber such as melting pulp and those composed of artificial cellulose fiber such as rayon or acetate. Softwood pulp, which has a longer fiber length than that of hardwood pulp, is preferably used in the light of function and cost performance. When crepe paper 15 surrounds the absorber 13 as in this embodiment, the crepe paper 15 is accordingly interposed between the liquid-permeable top sheet 11 and the absorber 13. Consequently, the crepe paper 15, which is excellent in absorbability, allows rapid diffusion of body fluid and prevents returning back of such menstrual blood or the like.

At the same time, the napkin main body 10 is provided with side nonwoven fabrics 14, 14 on the top both sides along the longitudinal direction over approximately the entire length of the napkin main body 10. The side nonwoven fabrics 14, 14 partially extend sideward to form wing-like flaps W, W together with parts of the liquid-impermeable bottom sheet 12 similarly extending sideward.

The side nonwoven fabric 14 is formed of a water-repellent nonwoven fabric or hydrophilic nonwoven fabric, according to the function that is emphasized. For example, when a function of preventing infiltration of menstrual blood, vaginal discharge, or the like or a function of increasing texture is emphasized, it is desirable to use a nonwoven fabric provided with water repellency by being coated with, for example, a silicon-based, paraffin-based, or alkyl chromic chloride-based water repellent agent. When absorbability of the wing-like flaps W, W for menstrual blood or the like is emphasized, it is desirable to use a hydrophilic nonwoven fabric imparted with hydrophilicity during a process of producing synthetic fiber by polymerization in the presence of a compound having a hydrophilic group, such as an oxidation product of polyethylene glycol, or by application of capillarity in which synthetic fiber is swollen or made porous by, for example, treating a surface with a metal salt such as stannic chloride for partially dissolving and making the surface porous and depositing a metal hydroxide.

As shown FIGS. 2 to 4, the main body having the liquid-permeable top sheet 11, the liquid-impermeable bottom sheet 12, and the absorber 13 interposed therebetween is provided with main body displacement-preventing adhesive layers 16, 16 . . . , for fixing to an undergarment on the side not brought into contact with the skin. The adhesive layers are formed in a plurality of lines, three lines in the example shown in the drawing, with an arbitrary application pattern. Furthermore, the wing-like flaps W, W are provided with wing displacement-preventing adhesive layers 17, 17 on the surface of the liquid-impermeable bottom sheet 12 side.

As an adhesive for forming the displacement-preventing adhesive layers 16 and 17, for example, an adhesive of which main ingredient is a styrene-based polymer, an adhesion-imparting agent, or a plasticizing agent is preferably used. Examples of the styrene-based polymer include styrene-ethylene-butylene-styrene block copolymers, styrene-butylene-styrene block copolymers, and styrene-isobutylene-styrene copolymers. These may be used alone or as a polymer blend of two or more thereof. Among them, from the standpoint of favorable thermal stability, the styrene-ethylene-butylene-styrene block copolymers are preferred. As the adhesion-imparting agent and the plasticizing agent, one that is solid at ordinary temperature is preferably used. Examples of the adhesion-imparting agent include C5-based petroleum resins, C9-based petroleum resins, dicyclopentadiene-based petroleum resins, rosin-based petroleum resins, polyterpen resins, and terpene phenol resins. Examples of the plasticizing agent include polymer plasticizing agents such as vinyl polymers and polyesters as well as monomer plasticizing agents such as tricresyl phosphate, dibutyl phthalate, and dioctyl phthalate.

[Structure of Napkin Sub-Body 20]

The napkin sub-body 20 is composed of any type of bottom sheet 22; a liquid-permeable top sheet 21 allowing prompt permeation of menstrual blood, vaginal discharge, or the like; and an absorber 23 interposed between both sheets and made of cotton pulp, synthetic pulp, or the like. The bottom sheet 22 and the liquid-permeable top sheet 21 are joined to each other in the circumference of the absorber 23 with an adhesive such as hot melt or by adhesion means such as heat sealing.

The details of the bottom sheet 22, the liquid-permeable top sheet 21, and the absorber 23 are the same as those of the napkin main body 10, and, therefore, only the items specific to the napkin sub-body 20 will be described in detail.

The napkin sub-body 20 is composed of a front portion 24 joined to the napkin main body 10 with an adhesive such as hot melt at a bleeding port-corresponding region and a back portion 25 extending backward than the front portion 24 and being dividable into right and left parts, a left part 25A and a right part 25B, by a dividing line 26 formed along the longitudinal direction at the center in the width direction of the sanitary napkin 1, the dividing line 26 extending along the back portion to the back end thereof. As shown in FIG. 5(B), the divided right and left parts can be spread toward the outsides in the width direction of the napkin main body 10 in such a manner that the boundary with the front portion 24 is at the base end of the dividing line 26. The back portion 25 in the individually packed state before use is not joined to the napkin main body 10. In addition, the portion along the dividing line 26 is not provided with the absorber 23, and thereby the bottom sheet 22 and the liquid-permeable top sheet 21 are joined to each other to form flaps.

Figure 5A:
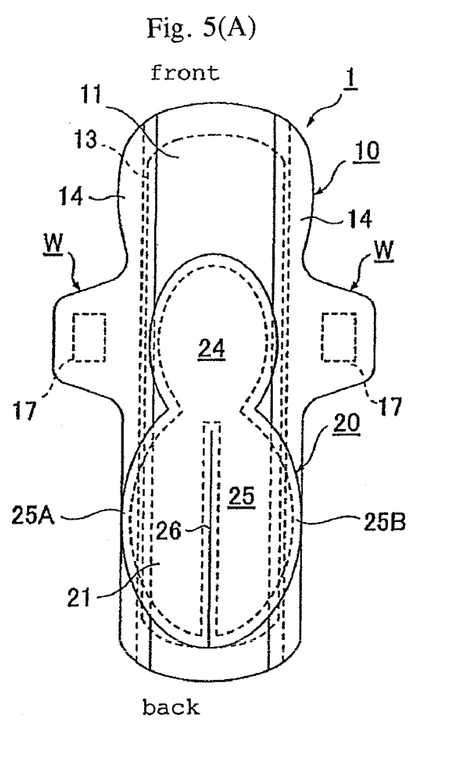
FIGS. 5(A) and 5(B) are developed views showing the sanitary napkin 1 in the individually packaged state (FIG. 5(A)) and in the usage state (FIG. 5(B)).
Figure 5B:
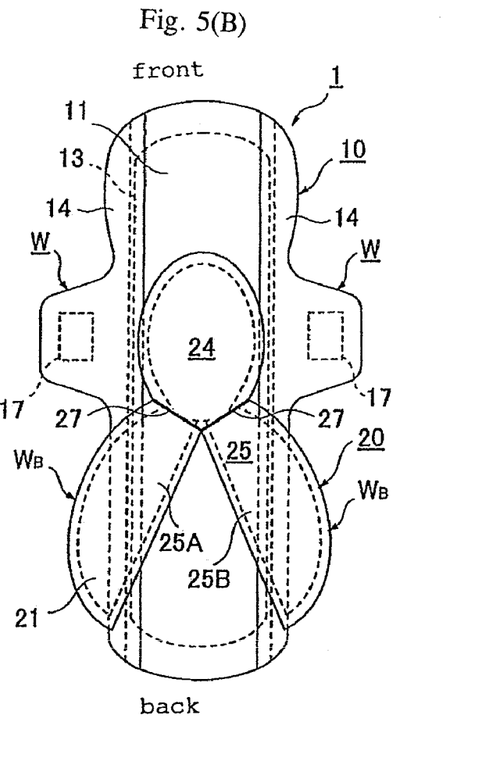

In order to put on the sanitary napkin 1, the right and left parts 25A and 25B of the back portion 25 in the individually packaged state before use as shown in FIG. 5(A) are spread to the respective sides from the boundary between the front portion 24 and the back portion 25 at the base end of the dividing line 26 so that the outside portions of the right and left parts 25A and 25B extend to the outsides in the width direction of the napkin main body 10 as shown in FIG. 5(B). The extending portions of the right and left parts 25A and 25B form hip-holding flaps $W_B$, $W_B$, and the lateral span of the hip-holding flaps $W_B$, $W_B$ can be optionally adjusted by adjusting the degree of spreading of the right and left parts 25A and 25B so as to fit the body of a user. Furthermore, in the boundary between the front portion 24 and the back portion 25, which boundary at the base end of the dividing line 26 when the right and left parts 25A and 25B are spread the front portion 24 and the back portion 25 at their juncture are folded in a wrinkle-like form as linear protrusions 27, 27 extending from the base end of the dividing line 26 to both side edges of the boundary between the front portion 24 and the back portion 25. The protrusions 27, 27 have a function of preventing menstrual blood or the like in the front portion 24 from flowing backward, which can inhibit diffusion of menstrual blood or the like to the back thereby to effectively prevent leakage from the back.

Figure 6:
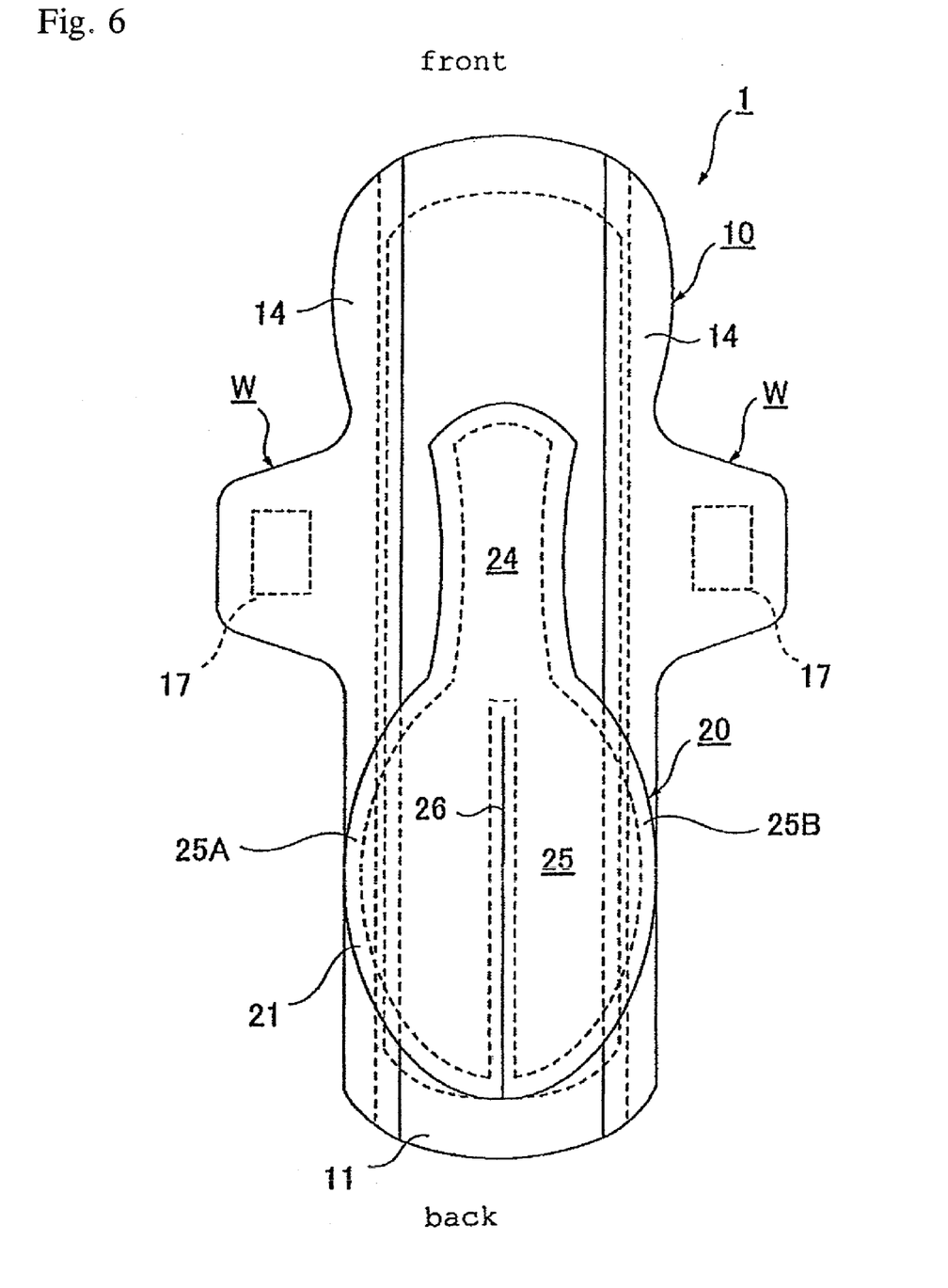
FIG. 6 is a developed view showing a modification (No. 1) of the sanitary napkin 1.

The front portion 24 is joined to the liquid-permeable top sheet 11 of the napkin main body 10 at the position corresponding to a bleeding or menstrual fluid port of the user, specifically, as shown in FIG. 1, at the central position in the width direction in the region corresponding in the length direction to the wing-like flaps W, W. Here, the front portion 24, as shown in FIG. 1, preferably has an approximately elliptical shape of which the long axis is in the front-back direction. In the thus approximately elliptical shape, the area overlapping the napkin main body 10 is enlarged in the bleeding part-corresponding region, and thereby the absorption amount is increased as a whole. In addition, the front portion 24 may have a concaved shape by concaving both sides as shown in FIG. 6 for decreasing uncomfortable feeling around the legs.

Figure 7A:
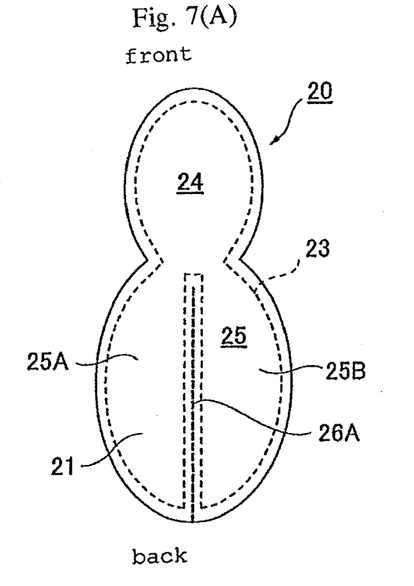
FIGS. 7(A) and 7(B) are developed views showing a modification of a napkin sub-body 20.
Figure 7B:
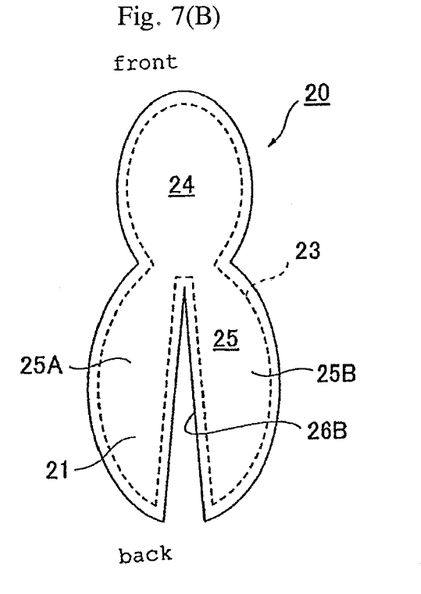

The dividing line 26 may be clean linear separation, for example an incision, between the right and left parts 25A and 25B in the sanitary napkin as provided to a user as shown in FIG. 1 or may be perforations 26A, as shown in FIG. 7(A), such that the right and left parts are not divided in the individually packaged state before use and are divided when used or the division between the right and left parts 25A and 25B may be a wedge-like notch 26B gradually spreading toward the back, as shown in FIG. 7(B).

Figure 8A:
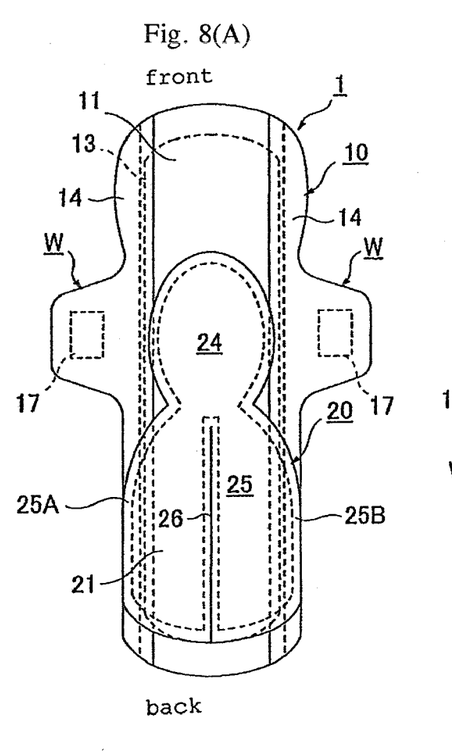
FIGS. 8(A) and 8(B) are developed views showing a modification (No. 2) of the sanitary napkin 1 in the individually packaged state (FIG. 8(A)) and in the usage state (FIG. 8(B)).
Figure 8B:
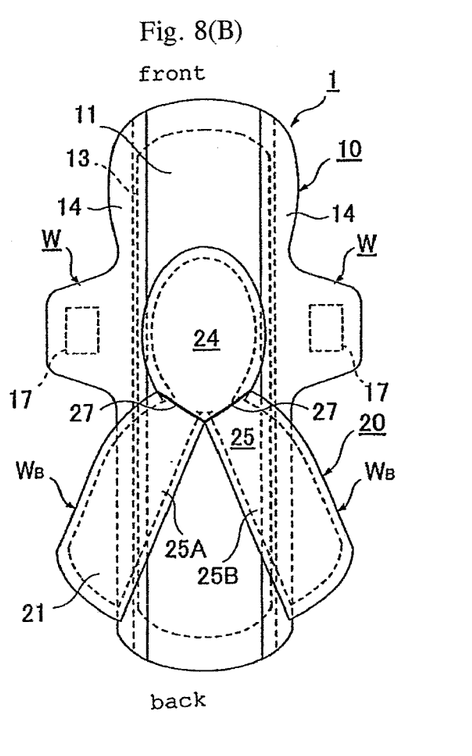

The back portion 25, as shown in FIG. 1, preferably has an approximately elliptical shape of which the long axis is in the front-back direction when it is in the individually packaged state before use, that is, in the state that the divided right and left parts 25A and 25B are positioned so as to face to each other and has a width equal to that of the napkin main body 10 lying under it. By doing so, when the right and left parts 25A and 25B of the back portion 25 are spread to both sides, hip-holding flaps $W_B$, $W_B$ can be formed so as to fit the buttocks. In addition, the back portion 25 in the individually packaged state, that is, in the state that the divided right and left parts 25A and 25B are arranged so as to face to each other, as shown in FIG. 8(A), may be shaped at their forward (front) edges as a curve approximately the shape of portions of an imaginary ellipse of which the long axis is in the front-back direction and a maximum width of the back portion 25 is approximately maintained toward the back end thereof. By doing so, as shown in FIG. 8(B), the formed hip-holding flaps $W_B$, $W_B$ can cover broader area.

Figure 9A:
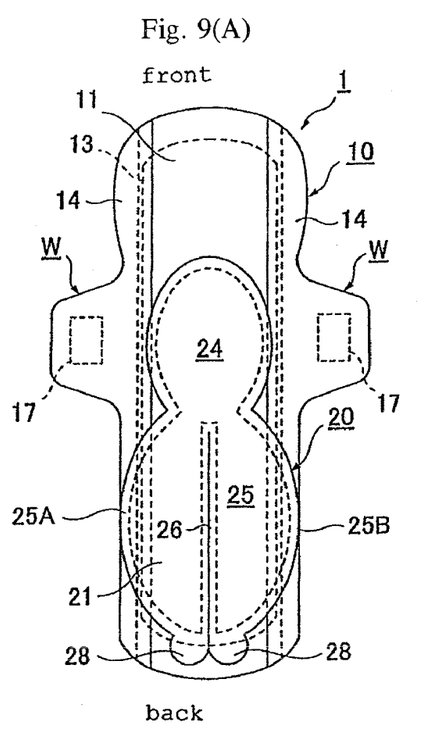
FIGS. 9(A) and 9(B) are developed views showing a modification (No. 3) of the sanitary napkin 1 in the individually packaged state (FIG. 9(A)) and in the usage state (FIG. 9(B)).
Figure 9B:
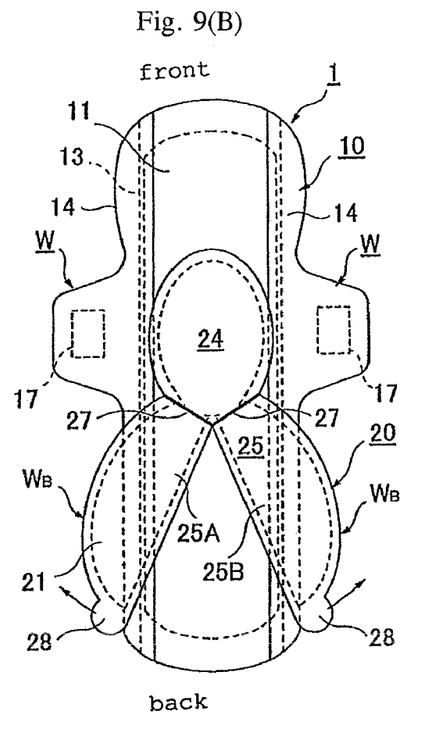

Furthermore, as shown in FIGS. 9(A) and 9(B), the right and left parts 25A and 25B of the back portion 25 may be provided with pinching tabs 28 extending toward the respective outsides. In the drawings, the pinching tabs 28 extending backward are formed at the back end of the back portion 25. By doing so, as shown in FIG. 9(B), a user can easily spread the right and left parts 25A and 25B of the back portion 25 to both sides.

Figure 10A:
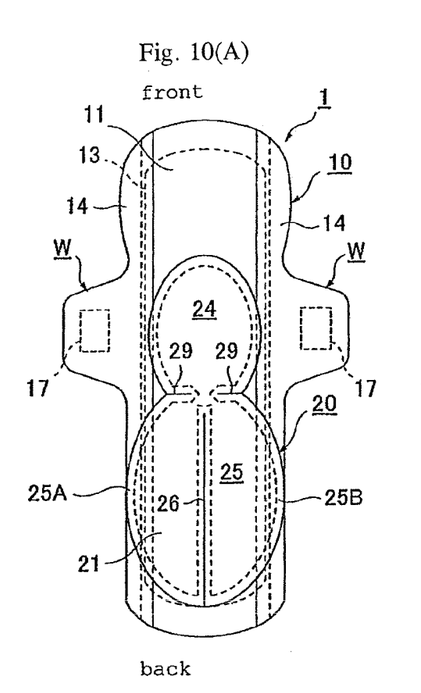
FIGS. 10(A) and 10(B) are developed views showing a modification (No. 4) of the sanitary napkin 1 in the individually packaged state (FIG. 10(A)) and in the usage state (FIG. 10(B)).
Figure 10B:
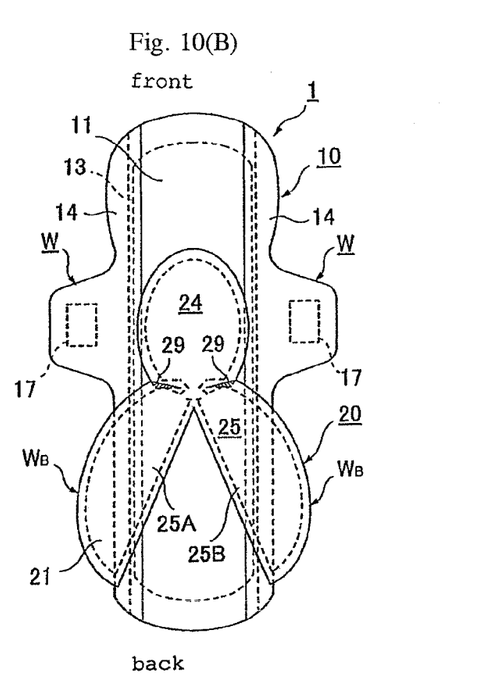

On the other hand, as shown in FIGS. 10(A) and 10(B), the boundary between the front portion 24 and the back portion 25 maybe respectively provided with incisions 29, 29 from both sides toward the inside in the width direction of the sanitary napkin 1. By providing the incisions 29, as shown in FIG. 10(B), when the right and left 25A and 25B of the back portion 25 are spread, the back portion 25 overlaps on the front portion 24 (shown with oblique lines in the drawing) without forming the protrusions 27 at the boundary between the front portion 24 and the back portion 25. Therefore, a function of preventing the flow of menstrual blood or the like can be obtained without causing uncomfortable feeling to the user. In addition, in the areas along the incisions 29, 29, the absorber 23 is not provided, and the bottom sheet 22 and the liquid-permeable top sheet 21 are joined to each other to form flaps. Here, the absorber 23 in the front portion 24 may be separated from that in the back portion 25 at the boundary, but even in such a case, the bottom sheet 22 and the liquid-permeable top sheet 21 are each formed in a substantially unified manner from the front portion 24 to the back portion 25.

Figure 11:
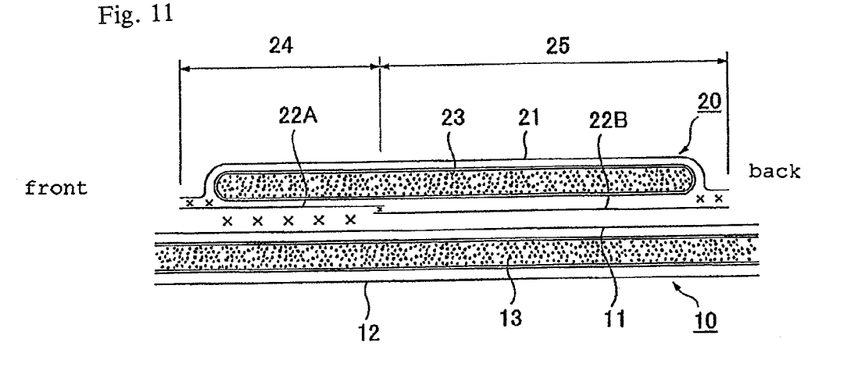
FIG. 11 is a fragmentary view taken along the line XI-XI of FIG. 1.

The bottom sheet 22 is combination of a liquid-permeable material and a liquid-impermeable material and is formed from the front portion 24 to the back portion 25 in a substantially unified manner. Specifically, in the example shown in FIG. 11, the bottom sheet 22 is composed of a liquid-permeable material 22A provided to the entire region of the front portion 24 and a liquid-impermeable material 22B provided to the entire or a part of the back portion 25. The liquid-permeable material 22A and the liquid-impermeable material 22B are joined together with overlapped margins at the boundary by an adhesive such as hot melt or by adhesion means such as heat sealing and are substantially constituted in a unified manner. Incidentally, when the liquid-impermeable material 22B is provided to a part of the back portion 25, the remaining region is provided with the liquid-permeable material 22A extending from the front portion 24.

Figure 12:
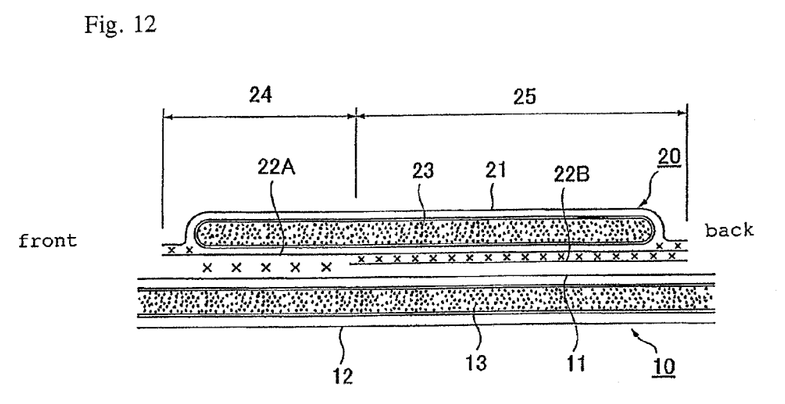
FIG. 12 is another modification of the fragmentary view taken along the line XI-XI of FIG. 1.

Furthermore, in the example shown in FIG. 12, the bottom sheet 22 is constituted in a substantially unified manner by disposing the liquid-permeable material 22A on the entire areas of the front portion 24 and the back portion 25, disposing the liquid-impermeable material 22B under the liquid-permeable material 22A in at least a part of the area of the back portion 25, and joining the liquid-impermeable material 22B to the liquid-permeable material 22A with an adhesive or adhesion means.

Thus, by disposing the liquid-impermeable material 22B to the entire or a part of the area of the back portion 25, the menstrual blood or the like absorbed by the absorber 23 is prevented from exuding to shorts even if the right and left parts 25A and 25B of the back portion 25 are spread to the outer sides than the napkin main body 10.

Figure 13A:
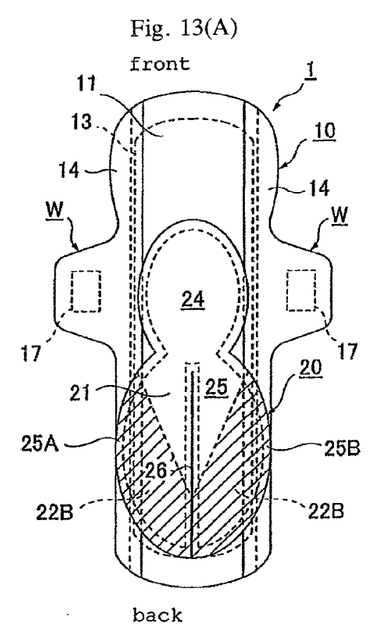
FIGS. 13(A) and 13(B) are developed views showing a modification (No. 5) of the sanitary napkin 1 in the individually packaged state (FIG. 13(A)) and in the usage state (FIG. 13(B)).
Figure 13B:
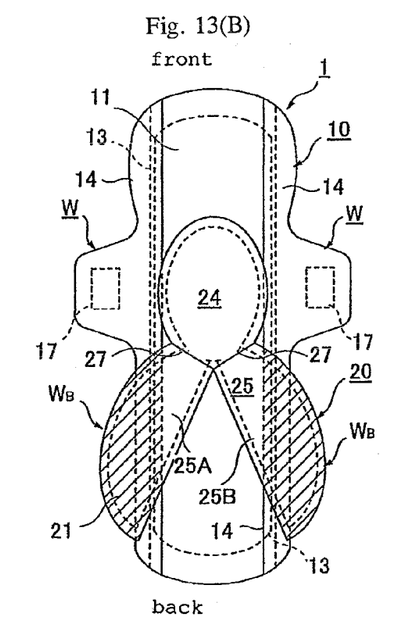

The configuration of a case that the liquid-impermeable material 22B is provided to a part of the back portion 25 will be described based on FIGS. 13(A) and 13(B). In this case, the liquid-impermeable material 22B of the back portion 25 is provided to at least the areas that will be located laterally outside the napkin main body 10 when the right and left parts 25A and 25B of the back portion 25 are spread to laterally outside the napkin main body 10, preferably to the areas that will be located laterally outside the absorber 13 of the napkin main body 10, more preferably to the areas that will be located laterally outside the inner end edges of the side nonwoven fabrics 14 of the napkin main body 10 (see FIG. 13(B)). By doing so, when the sanitary napkin 1 is used in the state that the right and left parts 25A and 25B are spread, the napkin 1 can be effectively utilized in a broad range without inhibiting menstrual blood or the like from being absorbed by the absorber 13 of the napkin main body 10, and even when the sanitary napkin 1 is used in the state that the right and left parts 25A and 25B are not spread, the napkin 1 can be effectively utilized in a broad range without inhibiting menstrual blood or the like from being absorbed by the absorber 13 at the portion of the back portions which, when the sanitary napkin 1 is worn, will be proximate to the bleeding port of the wearer.

Figure 14:
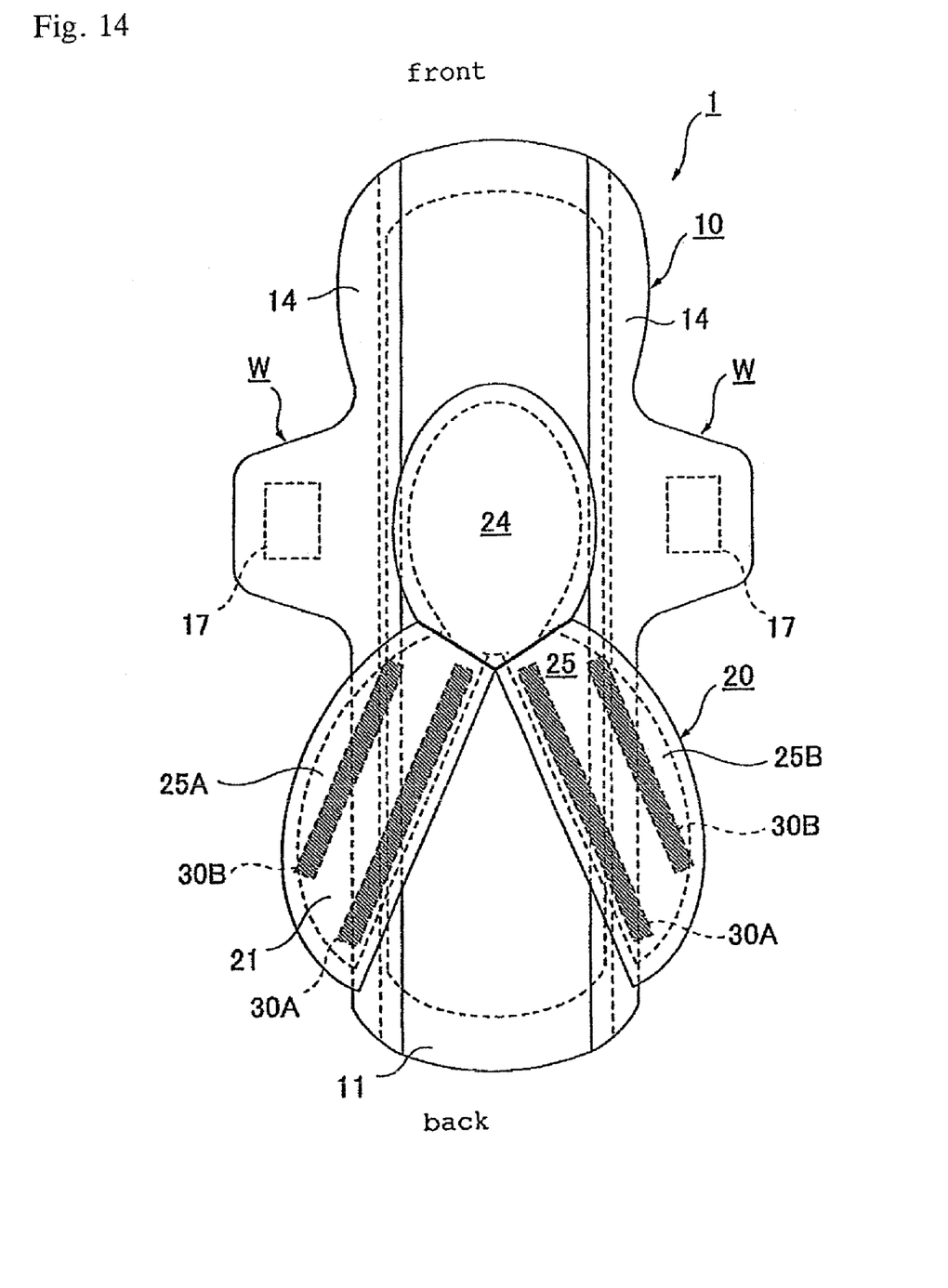
FIG. 14 is a developed view showing the usage state of a modification (No. 6) of the sanitary napkin 1.

On the other hand, as shown in FIG. 14, in order to maintain the hip-holding flaps $W_B$, $W_B$ formed by spreading the right and left parts 25A and 25B of the back portion 25 into the spread configuration, each of the right and left parts 25A and 25B is preferably provided with a plurality of lines of adhesive, two lines 30A and 30B in the example shown in the drawing, on the bottom sheet 22 side for letting the flaps adhere to the napkin main body 10 and shorts. In the example shown in the drawing, each inner adhesive strip 30A mainly has a function of bonding the right and left parts 25A and 25B to the napkin main body 10 and preventing absorbed menstrual blood or the like from exuding and leaking to the outside from a gap between the napkin main body 10 and the back portion 25 and also has a function of preventing formation of a gap between the napkin main body 10 and the back portion 25 thereby not to give uncomfortable feeling to a wearer. On the other hand, each outer adhesive layer 30B has a function of bonding the back portion 25 to shorts, in addition to a function of bonding the back portion 25 to the napkin main body 10. With this, displacement of the hip-holding flaps $W_B$ from shorts can be prevented, and also those from the napkin main body 10 to the shorts can be joined in a unified manner, which further firmly prevents displacement.

The adhesive layers 30A and 30B are each covered with a release material that is disposed to each of the right and left parts 25A and 25B. The release material may be in separate pieces to individually cover each of the adhesive strips 30A and 30B or may respective single pieces to cover each pair of strips 30A and 30B or one piece to cover all the strips. As the release material, paper or a plastic sheet subjected to release treatment on the surface that is brought into contact with the adhesive strips 30A and 30B by application or spray of a mold release liquid such as a silicon-based resin, a fluorine resin, or an ethylene tetrafluoride-based resin can be used.

Figure 15:
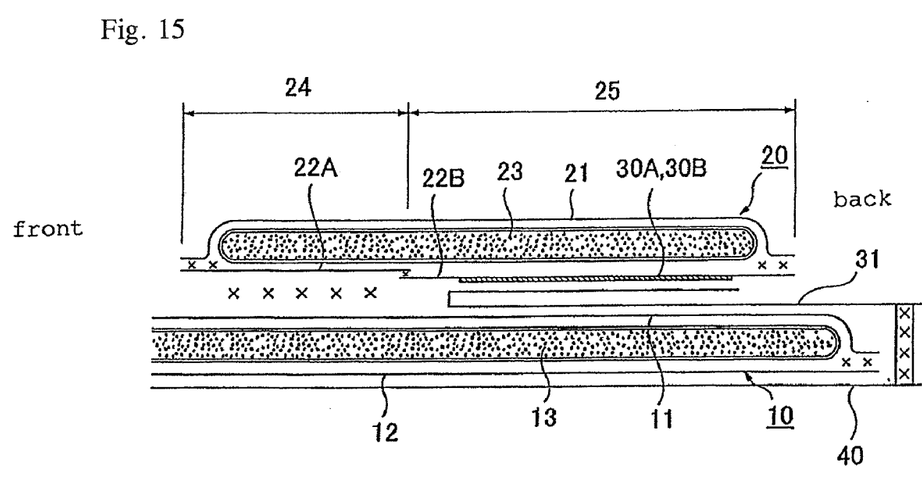
FIG. 15 is a fragmentary view taken along the line XV-XV of FIG. 1 in the individually packaged state.

Furthermore, as shown in FIG. 15, the release material 31 covering the adhesive layers 30A and 30B may be joined in a unified manner to the individual packaging material for individually packaging the sanitary napkin 1 so that the release material covering the adhesive layers 30A and 30B can be removed in one step when the individual packaging bag is opened and removed. Specifically, the back end of the release material 31 is joined to the back end of the individual packaging bag 40, and the release material 31 is folded back at the front end of the adhesive strips 30A and 30B. The folded-back portion covers the adhesive strips 30A and 30B. Here, the release material 31 may be composed of two pieces of the release material that are joined at the folded-back portion.

The invention claimed is:
1. An absorptive article comprising:
   an absorptive article main-body comprised of a top sheet, a liquid-impermeable bottom sheet, and an absorber interposed therebetween: and
   an absorptive article sub-body joined to an upper layer of the absorptive article main-body and comprised of a top sheet, a bottom sheet, and an absorber interposed therebetween, wherein
   the absorptive article sub-body is comprised of a front portion that is joined to the absorptive article main-body at a bleeding port-corresponding region and a back portion that is positioned behind the front portion and is comprised of right and left parts separated or separable substantially symmetrically about an actual or imaginary dividing line extending longitudinally in a front-back direction of the absorptive article from the back end of the center in the width direction of the absorptive article such that the right and left parts can, from an initial unspread state, be spread outward in a width direction of the absorptive article main-body from a boundary between the front portion and the back portion, a base end of the dividing line being located at said boundary, the bottom sheet of the absorptive article sub-body comprising a liquid-permeable material provided to the entire area of the front portion and a liquid-impermeable material provided to the entire or a part of the area of the back portion.

2. An absorptive article comprising:

an absorptive article main-body comprised of a top sheet, a liquid-impermeable bottom sheet, and an absorber interposed therebetween; and an absorptive article sub-body joined to an upper layer of the absorptive article main-body and comprised of a top sheet, a bottom sheet, and an absorber interposed therebetween, wherein the absorptive article sub-body is comprised of a front portion that is joined to the absorptive article main-body at a bleeding port-corresponding region and a back portion that is positioned behind the front portion and is comprised of right and left parts separated or separable substantially symmetrically about an actual or imaginary dividing line extending longitudinally in a front-back direction of the absorptive article from the back end of the center in the width direction of the absorptive article such that the right and left parts can, from an initial unspread state, be spread outward in a width direction of the absorptive article main-body from a boundary between the front portion and the back portion, a base end of the dividing line being located at said boundary, the bottom sheet of the absorptive article sub-body comprising a liquid-permeable material provided to the entire areas of the front portion and the back portion and a liquid-impermeable material provided to at least a part of the area of the back portion to form an under layer of the liquid-permeable material.

3. The absorptive article according to claim 1 or 2, wherein the liquid-impermeable material is provided to the back portion at least in the areas that will be located laterally outside the absorptive article main-body when the right and left parts are spread to extend laterally outside the absorptive article main-body.

* * * * *